United States Patent
Stam et al.

(10) Patent No.: US 11,058,837 B2
(45) Date of Patent: Jul. 13, 2021

(54) PATIENT TUBE SECUREMENT APPARATUS FOR SECURING A PATIENT TUBE TO A PATIENT

(71) Applicant: Fisher & Paykel Healthcare Limited, Auckland (NZ)

(72) Inventors: Simon Mordechai Stam, Auckland (NZ); Edwin Joseph Lyons, Auckland (NZ); Ibrahim Al-Tiay, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 746 days.

(21) Appl. No.: 15/129,500

(22) PCT Filed: Mar. 30, 2015

(86) PCT No.: PCT/NZ2015/050035
§ 371 (c)(1),
(2) Date: Sep. 27, 2016

(87) PCT Pub. No.: WO2015/152734
PCT Pub. Date: Oct. 8, 2015

(65) Prior Publication Data
US 2017/0173288 A1    Jun. 22, 2017

Related U.S. Application Data

(60) Provisional application No. 61/973,114, filed on Mar. 31, 2014.

(51) Int. Cl.
*A61M 16/04* (2006.01)
*A61M 25/02* (2006.01)

(52) U.S. Cl.
CPC .... *A61M 16/0497* (2013.01); *A61M 16/0461* (2013.01); *A61M 25/02* (2013.01);
(Continued)

(58) Field of Classification Search
CPC .............. A61M 16/0497; A61M 16/04; A61M 16/0666; A61M 16/0683; A61M 16/0461;
(Continued)

(56) References Cited

U.S. PATENT DOCUMENTS 3,924,636 A    12/1975 Addison
4,142,527 A    3/1979 Garcia
(Continued)

FOREIGN PATENT DOCUMENTS

WO    WO 2013/157960 A1    10/2013

OTHER PUBLICATIONS

International Search Report; PCT/NZ2015/050035; dated Jul. 17, 2015.

*Primary Examiner* — Margaret M Luarca
(74) *Attorney, Agent, or Firm* — Knobbe, Martens, Olson & Bear, LLP

(57) ABSTRACT

A patient tube securement apparatus is disclosed that may be used for oral or nasal intubation of a patient.
The apparatus may comprise an endotracheal tube securement apparatus for securing an endotracheal tube to a patient, the apparatus comprising a dermal patch arranged to be positioned on the skin of the patient, and at least one tube holder on the dermal patch.
The apparatus may comprise a patient tube securement apparatus for securing a patient tube to a patient, the apparatus comprising a dermal patch arranged to be positioned on the skin of the patient, and at least one tube holder on the dermal patch.
Examples are provided in which the tube holder is adjustably mounted on the dermal patch such that the position of the tube holder on the dermal patch can be adjusted without removing the dermal patch from the skin of the patient.

15 Claims, 3 Drawing Sheets

(52) U.S. Cl.
CPC . *A61M 2025/022* (2013.01); *A61M 2025/024* (2013.01); *A61M 2025/0266* (2013.01)

(58) Field of Classification Search
CPC . A61M 16/0488; A61M 25/02; Y10S 128/15; A61J 15/0053; A61J 15/0061
See application file for complete search history.

(56) References Cited

U.S. PATENT DOCUMENTS

| | | | | |
|---|---|---|---|---|
| 4,660,555 | A * | 4/1987 | Payton | A61M 16/0488 128/207.18 |
| 4,683,882 | A | 8/1987 | Laird | |
| 4,838,867 | A * | 6/1989 | Kalt | A61M 25/02 128/DIG. 26 |
| 5,743,885 | A * | 4/1998 | Hoerby | A61M 16/0497 128/DIG. 26 |
| 5,868,132 | A | 9/1999 | Winthrop et al. | |
| 6,050,263 | A * | 4/2000 | Choksi | A61M 16/0488 128/207.14 |
| 6,561,192 | B2 * | 5/2003 | Palmer | A61M 16/0488 128/207.14 |
| 6,866,652 | B2 * | 3/2005 | Bierman | A61M 25/02 128/DIG. 15 |
| 2001/0029954 | A1 | 10/2001 | Palmer | |
| 2006/0118120 | A1 | 6/2006 | Russo | |
| 2012/0167894 | A1 * | 7/2012 | O'Leary | A61M 16/0666 128/207.18 |
| 2015/0090255 | A1 | 4/2015 | Gulliver et al. | |

\* cited by examiner

PATIENT TUBE SECUREMENT APPARATUS FOR SECURING A PATIENT TUBE TO A PATIENT

INCORPORATION BY REFERENCE TO ANY PRIORITY APPLICATIONS

The entire contents of U.S. patent application 61/973,114 filed on 31 Mar. 2014 and from which priority is claimed are hereby incorporated by reference.

Any and all applications for which a foreign or domestic priority claim is identified in the Application Data Sheet as filed with the present application are hereby incorporated by reference under 37 CFR 1.57.

BACKGROUND OF THE INVENTION

Field of the Invention

The present invention relates to a patient tube securement apparatus for securing a patient tube to a patient. The patient tube securement apparatus may be used with, and/or may comprise part of, a respiratory assistance or treatment system. In one example the invention relates to securement apparatus for securing an endotracheal tube. In another example, the invention relates to securement apparatus for securing a patient feeding tube. More particularly, the present invention may comprise components that convey respiratory gases to/from a patient. In another aspect, the invention relates to a system or systems for positioning or securing a patient interface on a user.

Description of the Related Art

Respiratory assistance or treatment systems are used to provide respiratory gases to a patient. A respiratory system may include a humidification device to condition the gases provided to a patient. These gases may be heated or humidified prior to delivery. Gases are delivered to a patient via a tube in fluid communication with a patient interface. Gases delivered to patients at 100% relative humidity and 37° C. mimic the properties resulting from the transformation of air that occurs as it passes through the nose to the lungs. This promotes efficient gas exchange and ventilation in the lungs, aids defence mechanisms in the airways and increases patient comfort during treatment. Humidification of respiratory gases during invasive ventilation may be important to restore and maintain mucociliary clearance that is compromised by use of an invasive interface such as an endotracheal tube. Once a patient is intubated the invasive interface is secured in position during the patient treatment.

In other examples, a patient may be intubated in order to supply food/fluids/nutrients to the patient.

Although patient tube securement apparatus, such as for intubation, exist in the prior art, there can be problems associated with securing an invasive interface such as an endotracheal tube in position. A user may use medical tape or adhesive to secure the tube to a patient. This may require tape that covers a large portion of the face of the patient. Applying the tape to the patient may be a time consuming and complicated process. If a user desires to remove or adjust the securement apparatus, the tape must be removed which may compromise the integrity of the skin of the patient and may cause the patient discomfort. The tape must then be reapplied to the patient in the new position. A user may want to use a different therapy, or to wean a patient from invasive ventilation. A user may want to quickly secure the patient tube in position and move on to other patients. Prior art securement apparatus may struggle to meet the above features. Additionally, prior art apparatus may lead to unwanted extubation occurring during treatment, disrupting the therapy. In some cases damage may be caused to the skin of the patient. In some cases, the user may be securing the tube to an infant which may have particularly delicate skin exacerbating one or more of the above problems.

It is an object of the invention to overcome or ameliorate one or more of the above problems in the art, or at least to provide the public with a useful choice.

SUMMARY OF THE INVENTION

A patient tube securement apparatus is disclosed which may have improvements compared with those in the prior art. The securement apparatus may be used either for oral or nasal intubation of a patient. The securement apparatus may comprise a dermal patch which may attach to the skin of the patient, and a user interface which may releasably attach to the dermal patch. Thus, any rearrangement of the interface may be achieved by removing the user interface patch from the dermal patch, rather than the dermal patch from the skin of the patient. This may help to maintain the integrity of the skin of the patient, and may reduce damage to the skin of the patient. This may also provide flexibility should the user desire to alter the therapy, to wean the patient from invasive ventilation, or to adjust the tube during treatment, for example to prevent pressure sores forming on the lip. A rigid or partially rigid structure may attach to the user interface patch and extend across or at least partly across the face of the patient. The partially rigid structure may retain its structure while remaining flexible. An attachment arrangement may be located on the partially rigid structure and may be configured to attach to a tube. The attachment arrangement may be easily removable from the tube. In some cases the attachment arrangement may accommodate different movements, positions, or sizes of a patient. Thus, the attachment arrangement may increase the flexibility of the securement apparatus.

In one aspect of the invention there is provided an endotracheal tube securement apparatus for securing an endotracheal tube to a patient, the apparatus comprising a dermal patch arranged to be positioned on the skin of the patient, and at least one tube holder on the dermal patch, the tube holder being arranged to engage an endotracheal tube so that the endotracheal tube is positioned adjacent the patient in an operational position.

In accordance with another aspect of the invention there is provided a patient tube securement apparatus for securing a patient tube to a patient, the apparatus comprising a dermal patch arranged to be positioned on the skin of the patient, and at least one tube holder on the dermal patch, the tube holder being arranged to engage the patient tube so that the patient tube is positioned adjacent to the patient in an operational position, the tube holder being adjustably mounted on the dermal patch such that the position of the tube holder on the dermal patch can be adjusted without removing the dermal patch from the skin of the patient.

In one example, the apparatus is an endotracheal tube securement apparatus for securing an endotracheal tube to the face of a patient. In another example, the apparatus is a patient feeding tube securement apparatus for securing a patient tube to the face of a patient.

The dermal patch may comprise an attachment arrangement arranged to attach the apparatus in position on the skin of the patient. The attachment arrangement may comprise an adhesive pad or strip to adhere the dermal patch to the skin of the patient.

In some examples a plurality of tube holders are provided, each tube holder being at a different position on the dermal patch such that the position of the tube on the dermal patch can be selected by engaging the tube with a particular one of the plurality of tube holders.

The securement apparatus may comprise an adjuster arranged to enable the position of the or each tube holder to be adjusted relative to the dermal patch, without removing the dermal patch from the skin of the patient.

The tube holder may comprise an interface patch arranged to be located intermediate the tube holder and the dermal patch, the adjuster being arranged to enable the position of the interface patch on the dermal patch to be adjusted.

The adjuster may comprise any one or more of: a hook and loop fastener arrangement, and/or a snap-fit connector, and/or a releasable adhesive arranged such that the tube holder can be positioned and subsequently repositioned on the dermal patch.

In some embodiments the adjuster comprises at least one protrusion on one of the dermal patch and the tube holder, and at least one recess on the other of the dermal patch and the tube holder, the protrusion being received in the recess to retain the tube holder on the dermal patch. The adjuster may comprise a plurality of protrusions and/or a plurality of recesses.

The tube holder may be arranged to restrain the tube against movement in a direction parallel with the longitudinal axis of the tube, and/or against movement in a direction perpendicular with the longitudinal axis of the tube, and/or against movement in an angular direction relative to the dermal patch, that is, to restrain angular rotation of the longitudinal axis of the tube relative to the dermal patch. Similarly, the tube holder may be arranged to restrain the tube against movement in a selected direction, but to allow movement of the tube in a different selected direction.

The tube holder may comprise an arcuate retainer arranged to at least partially extend around the endotracheal tube.

The tube holder may comprise a resilient clip into which the tube is at least partially pressed to retain the endotracheal tube in the clip.

The tube holder may comprise an elongate restraint arranged to extend across the endotracheal tube to engage the endotracheal tube. The elongate restraint may comprise a hinge arranged to pivot over the endotracheal tube. The elongate restraint may comprise a strap arranged to extend over the endotracheal tube. The strap may be arranged to wrap around part of the endotracheal tube, with the strap extending in a direction parallel with the longitudinal axis of the tube.

The elongate restraint may comprise a release mechanism arranged to releasably engage with the dermal patch, such that, when released, the endotracheal tube is not engaged by the elongate restraint. The release mechanism may comprise a latch. The release mechanism comprises a bead on one of the tube holder and dermal patch, and a loop on the other of the tube holder and dermal patch, to receive the bead.

The tube holder may be adjustable so as to vary the retaining force applied to the endotracheal tube by the tube holder.

In some embodiments, the apparatus may comprise more than one dermal patch, and may comprise at least two dermal patches. Each dermal patch may be associated with a respective tube holder. In at least one example, the apparatus may further comprise a link member extending between and linking the two dermal patches, at least one tube holder being positioned on the link member. The at least one tube holder may be positioned on the link member intermediate the two dermal patches. A plurality of tube holders may be spaced apart along the link member.

In accordance with a further aspect of the invention, there is provided an intubation securement apparatus comprising:

a dermal patch comprising a patient side and an interface side, the patient side of said dermal patch configured to be positioned on the skin of said patient, a user interface patch comprising a patient side and an interface side, the patient side of said user interface patch configured to releasably attach to the interface side of said dermal patch, a partially rigid structure configured to attach to the interface side of said user interface patch, said partially rigid structure branching across the face of said patient and comprising an attachment mechanism in a central portion of the partially rigid structure to attach to a tube, wherein said tube is configured to be inserted into the nose or mouth of said patient.

Further aspects of the invention, which should be considered in all its novel aspects, will become apparent to those skilled in the art upon reading of the following description which provides at least one example of a practical application of the invention.

BRIEF DESCRIPTION OF THE DRAWINGS

These and other features, aspects, and advantages of the present invention will be described with respect to the following figures, which are intended to illustrate and not to limit the preferred embodiments.

DETAILED DESCRIPTION OF THE PREFERRED EMBODIMENT

Figure 1:
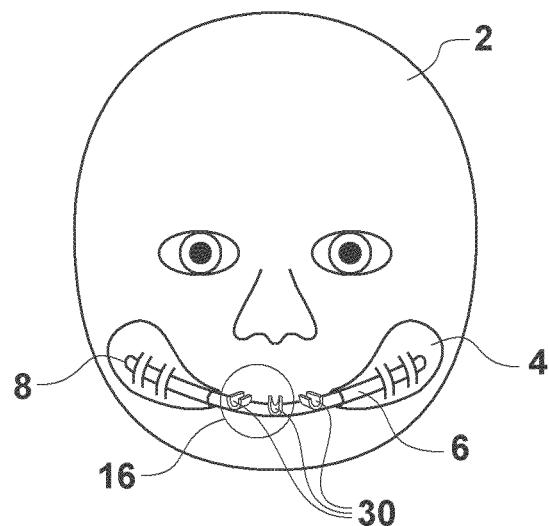
FIG. 1 is a front view of a patient tube securement apparatus in accordance with the invention, in use on a patient.

FIG. 1 shows a patient tube securement apparatus 4 provided with a tube holder 16 which is arranged to engage a patient tube (not shown), such as an endotracheal tube, so that the patient tube is positioned adjacent the patient in an operational position.

The patient tube securement apparatus 4 may be an endotracheal tube securement apparatus for securing an endotracheal tube to a patient, the apparatus 4 comprising a dermal patch 20 arranged to be positioned on the skin of the patient 2, and at least one tube holder 16 on the dermal patch 20. The tube holder 16 is arranged to engage an endotracheal tube (not shown) so that the endotracheal tube is positioned adjacent the patient 2 in an operational position.

The patient tube securement apparatus 4 may be a patient tube securement apparatus for securing a patient tube, such as an endotracheal tube or a patient feeding tube, to the patient. The tube holder 16 is adjustably mounted on the dermal patch 20 such that the position of the tube holder 16 on the dermal patch 20 can be adjusted without removing the dermal patch 20 from the skin of the patient 2.

In this example the patient tube securement apparatus 4 is arranged to position the patient tube on the face of a patient 2. The securement apparatus 4 comprises a way to secure an interface 8 of the apparatus 4 to the patient 2. This may be by use of a dermal patch 20 and a user interface patch 22, as shown in more detail in FIG. 3.

Figure 2:
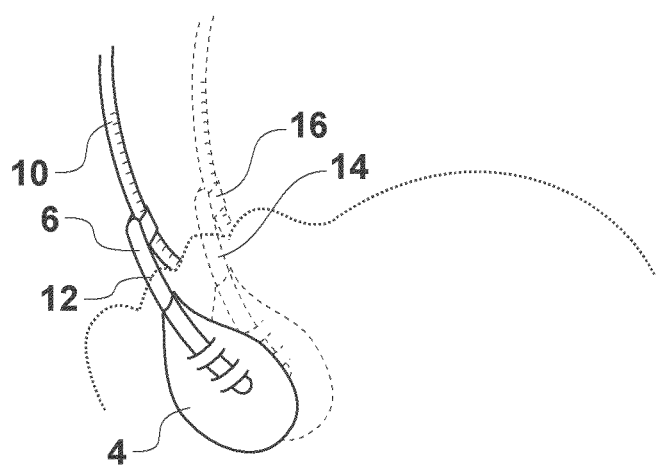
FIG. 2 is a side view of the securement apparatus of FIG. 1 in use on a patient in a first position, with an alternative position of the securement apparatus being shown in dashed lines.
Figure 3:
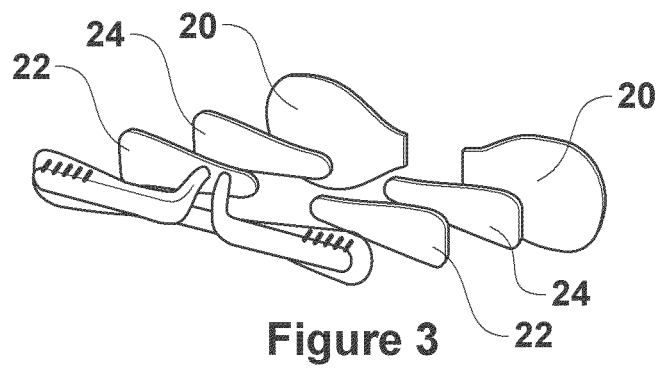
FIG. 3 is an exploded perspective view of a patient tube securement apparatus in accordance with the invention, including an attachment arrangement comprising an adhesive pad or strip for adhering the securement apparatus to a patient.

In the example of FIGS. 1 to 3, the patient tube securement apparatus 4 comprises a pair of dermal patches 20 and a pair of user interface patches 22, spaced apart by a link member which comprises a rigid or partially rigid structure 6. which may attach to the user interface patch 22 and branch across the face of the patient 2. The partially rigid structure 6 is provided with one or more attachment mechanisms being tube holders 16 to which a patient tube 10 attaches, as shown in FIG. 2.

The interface 8 as herein described may refer to a structure that supports the delivery of respiratory gases to the patient 2. This may refer to the user interface patch 22, the rigid or partially rigid structure 6, and the tube holder 16.

The dermal patch 20 as herein described refers to a relatively thin, plate like patch, pad, or similar, that uses an attachment arrangement, such as an adhesive for example, to attach the dermal patch 20 to the skin of the patient 2.

The user interface patch 22 as herein described refers to a relatively thin, plate like patch, pad, or similar, that attaches to the dermal patch 20 via a hook and loop mechanism, adhesive or the like. The user interface patch 22 is arranged to be located intermediate the tube holder 16 and the dermal patch 20 and an adjuster may be provided to enable the position of the interface patch 22 on the dermal patch 20 to be adjusted. The adjuster may comprise a hook and loop fastener arrangement, and/or one or more snap-fit connectors, and/or releasable adhesive arranged such that the tube holder 16 can be positioned and subsequently repositioned on the dermal patch 20.

The patient tube 10 as herein described may refer to any type of intubation tube and may refer to an invasive interface such as an endotracheal tube. In some embodiments the tube 10 may refer to an invasive interface such as a feeding tube, or the like.

The patient 2 as herein described may refer to an infant. In some embodiments the patient may refer to an adult or a child.

FIG. 2 shows that the securement apparatus 4 may be secured for use in an oral configuration 12 or in a nasal configuration 14. Thus, by attaching the securement apparatus 4 in a different location on the patient, for example on the patient's face, or by slightly rotating the securement apparatus 4, it may be used for different configurations. FIG. 2 shows the tube 10 as connecting via the attachment mechanism 16 to an upper side of the rigid or partially rigid structure 6. In some embodiments the tube 10 may approach a lower side of the rigid or partially rigid structure 6.

FIG. 3 shows the dermal patches 20 and the user interface patches 22 in more detail. Each dermal patch 20 comprises a patient side and an interface side. The patient side attaches to the skin of the patient 2, for example by a dermatologically sensitive adhesive such as a hydrocolloid. Each user interface patch 22 comprises a patient side and an interface side. The patient side of the user interface patch 22 attaches to the interface side of the dermal patch 20 via a releasable attachment or connection system 24. The user interface patch 22 may be attached to the dermal patch 20 using a hook and loop fastener arrangement, although any other suitable attachment system may alternatively or additionally be used. For example a snap fit type connector could be used whereby part of the interface patch 22 snap fits into a corresponding part of the dermal patch 20.

Thus, the user interface patch 22 may be releasably mounted on the dermal patch 20. The user interface patch 22 is also attached to the rigid or partially rigid structure 6 in the preferred embodiment, or to a cannula as is shown in FIG. 3, as part of the interface 8.

The releasable attachment between the dermal patch 20 and the user interface patch 22 allows a user to remove or rearrange the interface 8 once it has been attached to the patient 2. This removal or rearrangement of the interface 8 may be achieved without needing to remove the dermal patch 20 which adheres to the skin of the patient 2. Thus, the integrity of the skin of the patient 2 can be preserved, while maintaining the flexibility of the securement apparatus 4. This is particularly true if the patient 2 is an infant. The user interface patch 22 may thus be repositioned on the face of the patient 2 relative to the dermal patch 20. The repositioning of the user interface patch 22 may alter the contact area between the dermal patch 20 and the user interface patch 22.

FIGS. 1 and 2 show the rigid or partially rigid structure 6 that attaches to the user interface patch 22 and branches across the face of the patient 2. The rigid or partially rigid structure 6 forms part of the interface 8 that attaches to the dermal patch 20. The partially rigid structure 6 provides a surface on which to mount the tube holder 16. The partially rigid structure 6 may be sufficiently rigid such that it may retain its structure, while remaining flexible. Flexibility of the partially rigid structure 6 may be useful to accommodate movement of the patient 2, or to accommodate different positions of the patient 2. The flexibility of the partially rigid structure 6 may also reduce tugging or pulling on the securement apparatus 4 or the skin of the patient 2. In some embodiments the partially rigid structure 6 may swivel to aid in orientation of the tube 10. With particular reference to FIG. 2, this may be useful in the oral configuration 12 or the nasal configuration 10.

Different embodiments of the tube holder 16 are shown in FIGS. 4 to 7. It is to be understood that the embodiments shown are not intended to be limiting, but rather examples of how the tube holder 16 could be implemented. The tube holder 16 may be mounted onto the partially rigid structure 6, and may provide an attachment mechanism to attach the tube 10 to the interface 8.

Figure 4:
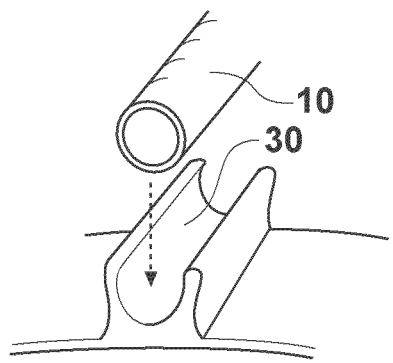
FIGS. 4-7 are enlarged views of part of a securement apparatus in accordance with the invention, each showing different features of a tube holder of the apparatus.

FIGS. 1 and 4 show the attachment mechanism 16 which comprises one or more clips 30. Each of the one or more clips 30 may be moulded in a single piece. The one or more clips 30 enable the tube 10 to be clipped into place on the partially rigid structure 6. Each clip 30 is therefore arranged to be resiliently deformable such that the clip 30 deforms as the tube 10 is pressed into the clip 30, and then reverts to its original shape when the tube is fully pressed in, so that part of the clip 30 engages the tube 10 to retain the tube 10 in the clip 30. Such a clip 30 may restrain the tube 10 against movement in all directions.

FIG. 1 shows that the one or more clips 30 may comprise multiple clips that may be mounted on the partially rigid structure 6 to accommodate different movements of the patient 2, different positions of the patient 2, or different sizes of patient or tube 10. For example, FIG. 1 shows that the one or more clips 30 comprises three clips that may provide a suitable embodiment of the attachment mechanism 16 for the tube 10 if the patient 2 lies in a supine position, or on either side. In this example, the clips 30 are spaced part along the length of the partially rigid structure 6, intermediate the pair of dermal patches 20. The tube 10 may be removed from one of the one or more clips 30 and reattached to a different one of the one or more clips 30 without interfering with any therapy being delivered to the patient. In some embodiments the one or more clips 30 may be mounted to a lower side of the partially rigid structure 6, which may allow the tube 10 to be attached to the lower side of the interface 8.

In some embodiments the tube holder 16 may comprise an elongate restraint such as a hinge. The hinge may close around the tube 10, securing it in position on the tube holder 16.

Figure 5:
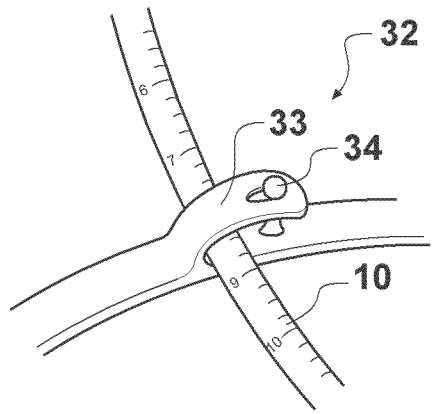

FIG. 5 is an example of the tube holder 16 which comprises an elongate restraint comprising a button arrangement 32. The button arrangement 32 comprises a strap 33 that releasably engages with a button 34. The strap 33 is arranged to extend over the tube 10 and be secured to the interface 8 via a button or clip 32A that passes through an aperture in the distal end of the strap 33. The button arrangement 32 may secure the tube 10 while allowing limited movement of the tube 10.

Figure 6:
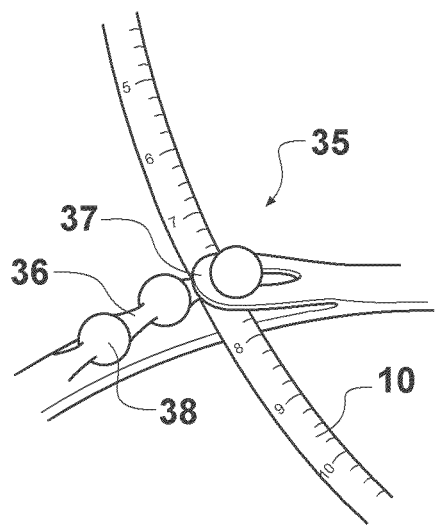

FIG. 6 is an example of an elongate restraint which comprises a beaded arrangement 35 that comprises a beaded strap 36 and a loop 37. The beaded strap 36 comprises one or more beads 38. The loop 37 is configured to engage with the one or more beads 38 of the beaded strap 36. FIG. 6 shows an example where the beaded strap 36 comprises multiple beads 38. The beaded strap 36 allows the tube 10 to be secured while maintaining limited movement of the tube 10 beneath the beaded strap 36. Limited movement of the tube 10 within the beaded arrangement 35 may provide flexibility to compensate for movement of the patient 2, and allow for different positions of the patient 2 without interfering with the therapy.

Figure 7:
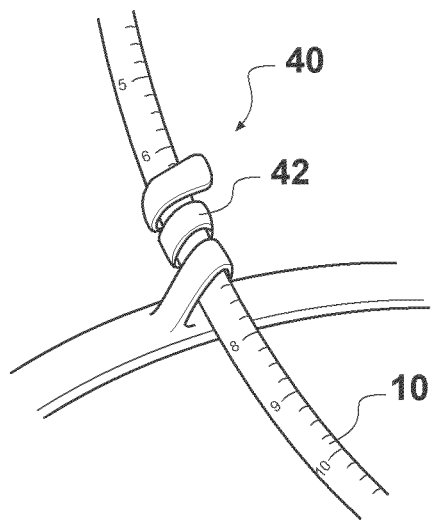

FIG. 7 is an example of an elongate restraint comprising a strapping arrangement 40 comprising a wrap 42. The wrap 42 is configured to wrap around the tube 10 in the direction of the longitudinal axis of the tube 10 and secure the tube 10 in position. In some embodiments the wrap 42 may comprise a side configured to adhere to the tube 10 using an adhesive. In some embodiments a hook and loop mechanism on one side of the wrap 42 may be configured to interact with a corresponding hook and loop mechanism on the other side of the wrap 42 to secure the tube 10. In some embodiments, friction between the tube 10 and the strapping arrangement 40 may be sufficient to secure the tube 10. It is to be understood that combinations of the above embodiments may also fall within the scope of the invention.

The securement apparatus 4 may be applied to the patient 2 following intubation of the patient 2. If the user wishes to rearrange or move the tube 10 following intubation of the patient 2 they can either move the securement apparatus 4 or the interface 8 while maintaining the tube 10 position, or the tube 10 can be detached from the tube holder 16 as the securement apparatus 4 or the interface 8 is moved, and then the tube 10 can be reattached to the tube holder.

In some cases the user may replace the securement apparatus 4 with a non-invasive interface. This could be done whilst leaving the dermal patch or patches 20 in place on the skin of the patient. A non-invasive interface as herein described may refer to a nasal cannula, mask, nasal pillows, or the like. In some cases a non-invasive interface may be removed and the securement apparatus 4 may be applied or re-applied to the patient 2.

In some embodiments the interface 8 may be removed from the patient 2 during, at the end of, or in between, therapies. In these embodiments the dermal patch 20 may remain on the face of the patient 2. A complimentary non-invasive interface may then attach to the dermal patch 20. Thus in some cases, the dermal patch 20 may not need to be removed from the skin of the patient 2 between therapies. This may help to maintain the integrity of the skin of the patient 2. Similarly if the patient 2 is changed from a non-invasive therapy to an invasive therapy, a complimentary non-invasive interface may be removed and may leave the dermal patch 20 of the complimentary non-invasive interface attached to the skin of the patient 2. This allows the interface 8 to be applied directly to the patient 2.

In some embodiments the securement apparatus 4 may come in different sizes to suit the patient 2. In some embodiments, the sizing of the securement apparatus 4 may match the sizing of a complimentary non-invasive interface. This may allow a user to more quickly identify the correct size of securement apparatus 4 that should be used. A range of colours or shades may alternatively or additionally be used to visually indicate sizing to the user.

The securement apparatus 4 may be used for oral or nasal intubation as required, and may indeed be provided with more than one tube holder 16, one in a position on the interface 8 suitable for oral intubation, and another tube holder 16 in a different position on the interface 8 suitable for nasal intubation. Alternatively a single tube holder 16 may be provided, the tube holder 16 being movable relative to the dermal patch 20 to allow the tube holder 16 to be in a position suitable for oral and nasal intubation. The tube holder 16 may be rotationally adjustable on the interface 8 such that the tube holder 16 may be rotated relative to the dermal patch 20 to the required orientation.

Whilst embodiments have been described and illustrated showing the securement apparatus 4 in an operational position on the face of a patient, the securement apparatus 4 could equally be used in operational positions elsewhere on the patient, for example on the neck or chest of the patient.

Whilst embodiments have been described and illustrated showing the securement apparatus 4 comprising a pair of dermal patches 20/interface patches 22 and a partially rigid structure 6 comprising a link member linking the pair of interface patches 22, the apparatus 4 may comprise only a single dermal patch 20/interface patch 22, with one or more tube holders 12 being mounted on the single interface patch 22.

The rigid or partially rigid structure 6 may be flexibly or movably mounted on the interface 8 to allow for a limited movement between the patient tube 10 and the patient 2 in use.

The dermal patch 20 and/or the interface patch 22 may be formed of a soft plastic and/or a silicone material or a combination of such materials. Each patch 20, 22 may be of laminate construction formed from layers of a material or combinations of materials. The material or materials may be selected to give the desired combination of strength, weight and flexibility.

It is to be understood that the securement apparatus 4 described is not limited to an endotracheal tube but may be applied to other forms of invasive treatment requiring a patient tube, such as but not limited to, a patient feeding tube, or the like.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to".

Reference to any prior art in this specification is not, and should not be taken as, an acknowledgement or any form of suggestion that that prior art forms part of the common general knowledge in the field of endeavour in any country in the world.

The invention may also be said broadly to consist in the parts, elements and features referred to or indicated in the specification of the application, individually or collectively, in any or all combinations of two or more of said parts, elements or features.

Where, in the foregoing description reference has been made to integers or components having known equivalents thereof, those integers are herein incorporated as if individually set forth.

It should be noted that various changes and modifications to the presently preferred embodiments described herein will be apparent to those skilled in the art. Such changes and modifications may be made without departing from the spirit and scope of the invention and without diminishing its attendant advantages. For instance, various components may be repositioned as desired. It is therefore intended that such changes and modifications be included within the scope of the invention. Moreover, not all of the features, aspects and advantages are necessarily required to practice the present invention. Accordingly, the scope of the present invention is intended to be defined only by the claims that follow.

What is claimed is:

1. An endotracheal tube securement apparatus for securing an endotracheal tube to a patient, the apparatus comprising:
    a pair of dermal patches to be positioned on the skin of the patient, each dermal patch comprising a patient side facing the skin of the patient and an interface side opposite the patient side;
    a pair of user interface patches, each user interface patch comprising a patient side and an interface side, the patient side of each user interface path configured to releasably attach to the interface side of one of the pair of dermal patches; and
    a link member extending between the pair of user interface patches, the link member comprising a first end on the interface side of one of the pair of user interface patches and a second end on the interface side of the other one of the pair of user interface patches, the link member further comprising at least one tube holder, the at least one tube holder comprising a first end and a second end, wherein the link member is attached to the at least one tube holder at a position between the first end and the second end of the at least one tube holder, the at least one tube holder being arranged to engage an endotracheal tube so that the endotracheal tube is positioned adjacent the patient in an operational position;
    wherein the apparatus comprises a nasal configuration in which the pair of user interface patches are positioned at a first location relative to the pair of dermal patches to enable the at least one tube holder to hold the patient tube in a nose of the patient,
    wherein the apparatus comprises an oral configuration in which the pair of user interface patches are positioned at a second location relative to the pair of dermal patches to enable the at least one tube holder to hold the patient tube in a mouth of the patient.

2. The apparatus of claim 1 wherein each dermal patch comprises an adhesive.

3. The apparatus of claim 1 wherein the at least one tube holder comprises a plurality of tube holders, each tube holder being at a different position on the link member such that the position of the endotracheal tube can be selected by engaging the endotracheal tube with a particular one of the plurality of tube holders.

4. The apparatus of claim 1 wherein the position of the at least one tube holder is adjustable relative to the pair of dermal patches, without removing the pair of dermal patches from the skin of the patient.

5. The apparatus of claim 1 wherein the link member can be positioned and subsequently repositioned on the pair of dermal patches.

6. The apparatus of claim 1 further comprising at least one protrusion on one of the pair of dermal patches and the at least one tube holder, and at least one recess on the other of the pair of dermal patches and the at least one tube holder, the protrusion being received in the recess to retain the at least one tube holder on the pair of dermal patches.

7. The apparatus of claim 1 wherein the at least one tube holder is arranged to restrain the tube against movement.

8. The apparatus of claim 1 wherein the at least one tube holder comprises an arcuate retainer arranged to at least partially extend around the endotracheal tube.

9. The apparatus of claim 1 wherein the at least one tube holder comprises a resilient clip into which the tube is at least partially pressed to retain the endotracheal tube in the clip.

10. The apparatus of claim 1 wherein the at least one tube holder comprises an elongate restraint arranged to extend across the endotracheal tube to engage the endotracheal tube.

11. The apparatus of claim 1 wherein the at least one tube holder is adjustable so as to vary the retaining force applied to the endotracheal tube by the at least one tube holder.

12. A patient tube securement apparatus for securing a patient tube to a patient, the apparatus comprising:
    a pair of dermal patches arranged to be positioned on the skin of the patient, each of the pair of dermal patches comprising a patient side facing the skin of the patient and an interface side opposite the patient side;
    a pair of user interface patches, the pair of user interface patches being separate from one another, wherein each user interface patch comprises a patient side and an interface side, the patient side of each user interface patch configured to releasably attach to the interface side of one of the pair of dermal patches; and
    at least one tube holder positioned between the pair of dermal patches, the at least one tube holder being arranged to engage the patient tube so that the patient tube is configured to be positioned into the nose or the mouth of the patient, the at least one tube holder being adjustably mounted such that the position of the at least one tube holder can be adjusted without removing the pair of dermal patches from the skin of the patient,
    wherein the apparatus comprises a nasal configuration in which the pair of user interface patches are positioned at a first location relative to the pair of dermal patches to enable the at least one tube holder to hold the patient tube in the nose of the user,
    wherein the apparatus comprises an oral configuration in which the pair of user interface patches are positioned at a second location relative to the pair of dermal patches to enable the at least one tube holder to hold the patient tube in the mouth of the user.

13. The apparatus of claim 12 being an endotracheal tube securement apparatus for securing an endotracheal tube to the face of the patient.

14. The apparatus of claim 12 being a patient feeding tube securement apparatus for securing a patient tube to the face of the patient.

15. An intubation securement apparatus comprising:
a dermal patch comprising a patient side and an interface side, the patient side of said dermal patch configured to be positioned on the skin of said patient, wherein the dermal patch comprises a first dimension from an upper edge of the dermal patch to a lower edge of the dermal patch,
a user interface patch comprising a patient side and an interface side, the patient side of said user interface patch configured to releasably attach to the interface side of said dermal patch, wherein the user interface patch comprises a second dimension from an upper edge of the user interface patch to a lower edge of the user interface patch, the second dimension being less than the first dimension,
a partially rigid structure configured to attach to the interface side of said user interface patch, said partially rigid structure branching across the face of said patient and comprising an attachment mechanism in a central portion of the partially rigid structure to attach to a tube,
wherein said tube is configured to be inserted into the nose or the mouth of the patient,
wherein the partially rigid structure is configured to be adjustable so that the intubation securement apparatus is changeable between a nasal configuration and an oral configuration without removing the dermal patch;
wherein in the nasal configuration, the user interface patch is positioned at a first location relative to the dermal patch to enable the partially rigid structure to hold the tube in the nose of the patient,
wherein in the oral configuration, the user interface patch is positioned at a second location relative to the dermal patch to enable the partially rigid structure to hold the tube in the mouth of the patient.

* * * * *